(12) United States Patent
Rogers et al.

(10) Patent No.: US 8,262,717 B2
(45) Date of Patent: Sep. 11, 2012

(54) VESTIBULAR STIMULATION APPARATUS AND ASSOCIATED METHODS OF USE

(75) Inventors: Lesco L. Rogers, Raleigh, NC (US); Lanty L. Smith, Raleigh, NC (US)

(73) Assignee: Scion Neurostim, LLC., Raleigh, NC (US)

( * ) Notice: Subject to any disclaimer, the term of this patent is extended or adjusted under 35 U.S.C. 154(b) by 339 days.

(21) Appl. No.: 12/669,684

(22) PCT Filed: Aug. 1, 2008

(86) PCT No.: PCT/US2008/071935
§ 371 (c)(1),
(2), (4) Date: Apr. 19, 2010

(87) PCT Pub. No.: WO2009/020862
PCT Pub. Date: Feb. 12, 2009

(65) Prior Publication Data
US 2010/0211142 A1 Aug. 19, 2010

Related U.S. Application Data

(60) Provisional application No. 60/953,700, filed on Aug. 3, 2007.

(51) Int. Cl.
*A61F 7/12* (2006.01)
(52) U.S. Cl. .................................. 607/113; 607/112
(58) Field of Classification Search .............. 606/27–29; 607/96, 112, 113
See application file for complete search history.

(56) References Cited

U.S. PATENT DOCUMENTS

| | | | |
|---|---|---|---|
| 4,860,748 A * | 8/1989 | Chiurco et al. | 607/96 |
| 8,083,786 B2 | 12/2011 | Gafni et al. | |
| 2003/0195588 A1 | 10/2003 | Fischell et al. | |
| 2008/0264464 A1 * | 10/2008 | Lee et al. | 136/201 |

FOREIGN PATENT DOCUMENTS
WO WO 2007/051911 A1 5/2007

OTHER PUBLICATIONS

International Search Report and Written Opinion, PCT/US2008/071935, mailed Jul. 16, 2009.
Coats AC. Temperature effects on the peripheral auditory apparatus. Science. Dec. 10, 1965; 150(702): 1481-1483.
Kolev "How caloric vestibular irritation influences migraine attacks" *Cephalalgia* 10:167-169, 1990.
Ried "Asymmetries of Vestibular Dysfunction in Major Depression" *Neuroscience* 144:128-134, 2007.

* cited by examiner

*Primary Examiner* — Roy Gibson
(74) *Attorney, Agent, or Firm* — Myers Biegel Sibley & Sajovec, P.A.

(57) ABSTRACT

A device and associated method for providing vestibular stimulation to an individual includes active elements positioned on or proximate an ear insert. The active elements include but are not limited to at least one electrode, at least one thermometer, and at least one thermoelectric transducer. The device includes a computerized control module regulating the active elements. The device incorporates an ear insert that allows the active elements to engage the individual's ear canal and therefore access the individual's vestibular system. Vestibular stimulation applied to the individual is customized for directly stimulating desired regions of the brain for therapeutic or diagnostic purposes. In a preferred embodiment, the device provides vestibular stimulation sufficient to promote physiological changes in the individual, the changes selected from the group consisting of circadian temperature cycle time shifts, ascorbic acid production, serotonin production, acetylcholine production, histamine production, and heat shock protein production.

33 Claims, 8 Drawing Sheets

VESTIBULAR STIMULATION APPARATUS AND ASSOCIATED METHODS OF USE

RELATED APPLICATIONS

This application is a 35 U.S.C. §371 national phase application of PCT Application PCT/US2008/071935, filed Aug. 1, 2008, and published in English on Feb. 12, 2009, as International Publication No. WO 2009/020862, and which claims the benefit under 35 U.S.C. §119(e) of U.S. Provisional Patent Application Ser. No. 60/953,700, filed Aug. 3, 2008, the disclosure of each of which is incorporated herein by reference in its entirety.

FIELD OF THE INVENTION

The present invention concerns an apparatus and associated methods useful for delivering vestibular stimulation to the vestibular system of an individual, thereby inducing physiological changes in the individual's body.

BACKGROUND OF THE INVENTION

Caloric vestibular stimulation has long been known as a diagnostic procedure for testing the function of the vestibular system. In the traditional hospital setting, water caloric tests are still used to assess levels of consciousness during acute or chronic brain injury. The brain injury may be due to head trauma or a central nervous system event such as a stroke. Other brain injuries occur in the presence of metabolic abnormalities (e.g., kidney disease, diabetes), seizures, or toxic levels of controlled substances or alcohol. Common techniques to determine consciousness involve simple irrigation of the ear canal with heated (or chilled) water or air. The typical setting for these measures is the hospital emergency room, but water caloric tests are also used in intensive care units and in treating patients admitted to medical or surgical floors. Cold irrigation has also been used in studies testing stroke victims' temporary recovery of cognitive impairments. See Schiff and Pulver, "Does Vestibular Stimulation Activate Thalamocortical Mechanisms that Reintegrate Impaired Cortical Regions?" *Proceedings of the Royal Society of London (B)* 266: 421-423 (1999).

To reduce the inconvenience of cleaning spilled irrigation fluid, "closed flow" apparatuses, in which an inflatable balloon was configured to be inserted into the ear canal and contain the irrigation fluid, were developed. See, e.g., U.S. Pat. No. 4,190,033 to Foti and U.S. Pat. No. 4,244,377 to Grams. Another more recent development includes electrical stimulation to the vestibular labyrinth by galvanic current applied to the mastoid region. In one study, the current was applied to one or both sides of the head either independently or simultaneously. Ocular monitoring showed levels of brain activity based on eye movement associated with vestibular stimulation. See, Schlosser, et al., "Using Video-Oculography for Galvanic Evoked Vestibulo-Ocular Monitoring in Comatose Patients," *Journal of Neuroscience Methods* 145: 127-131 (2005).

More recently, caloric vestibular stimulation has been applied to other purposes. O. Kolev, "How caloric vestibular irritation influences migraine attacks," *Cephalalgia* 10, 167-9 (1990) describes the relief of migraine symptoms by cold caloric vestibular stimulation.

D. Bachtold et al., "Spatial- and verbal-memory improvement by cold-water caloric stimulation in healthy subjects," *Exp Brain Res* 136: 128-132 (2001) (published online 16 Nov. 2000), describe the results noted in the title. In their final paragraph they state "activation arising from vestibular stimulation of the contralesional ear may transiently improve neglected patients' symptoms," and that their findings indicate "caloric stimulation may improve lateralized cognitive functions whether they are spatial in nature or not."

U.S. Pat. No. 6,748,275 to Lattner, "Vestibular Stimulation System and Method" describes an apparatus that can be used to "augment or control a patient's respiratory function . . . induce sleep, and/or counteract vertigo." (column 3, lines 55-60). The apparatus can be invasive or noninvasive (column 7, lines 45-50), and the stimulation can be completed by one or more of electrical, mechanical, magnetic, or thermal stimulation (column 7, lines 50-55). The thermal stimulation can be heated or chilled liquid (column 8, line 65).

US Patent Application Publication No. 2003/0195588 to Fischell et al., "External ear canal interface for the treatment of neurological disorders," also describes a system for treating neurological disorders. Disorders suggested for treatment include dizziness, vertigo, seasickness and travel sickness (jet lag) (paragraph 17), as well as seizure (paragraph 11).

Y. Yamamoto et al., "Noisy vestibular stimulation improves autonomic and motor responsiveness in central neurodegenerative disorders," *Ann Neurol.* 58: 175-181 (2005), state that "noisy GVS (galvanic vestibular stimulation) is effective in boosting the neuro-degenerative brains of patients with multi system atrophy or Parkinson's disease, or both, including those unresponsive to standard levodopa therapy . . . " (abstract).

V. Ramachandran et al. "Rapid Relief of Thalamic Pain Syndrome Induced by Vestibular Caloric Stimulation," *Neurocase*, iFirst, 1-4 (2007), describes the use of caloric vestibular stimulation in the treatment of pain.

A general review of the various uses of caloric vestibular stimulation is given in S. Miller and T. Ngo, "Studies of caloric vestibular stimulation: implications for the cognitive neurosciences, the clinical neurosciences and neurophilosophy," *Acta Neuropsychiatrica* 19: 183-203 (2007).

The ear canal is sensitive to foreign objects (U.S. Pat. No. 4,244,377 to Grams at column 2 line 28). Completely-in-the-canal ("CIC") hearing aids sometimes resolve this problem by producing the hearing aids as soft, resilient, individually cast devices (see, e.g., U.S. Pat. No. 6,249,587 to Clavadetscher et al.), but individual casting of a device can be slow, complicated, and costly. Hence, there is a need for new devices that are useful for delivering vestibular stimulation and other therapies via the ear canal in a manner that is both comfortable and convenient for the wearer.

It is also significant that engaging the ear canal and the inner ear via an insert makes possible numerous therapies and diagnostic techniques directed to the brain. Previous studies have highlighted the therapeutic effects of inducing changes in brain chemistry and blood chemistry by stimulating particular regions of an individual's brain tissue. For example, the suprachiasmatic nucleus (the "SCN") area of the brain (within the hypothalamus) controls an individual's circadian cycle, keeping multiple body rhythms on a synchronized 24-hour clock (e.g., the sleep-wake cycle, temperature fluctuations, endocrine activity, and metabolic activity). See, Turek et al., "Current Understanding of the Circadian Clock and the Clinical Implications for Neurological Disorders," *Archives of Neurology;* 58: 1781-1787 (2001). This "core clock" controls "electrical firing" and "gene expression" that dominate the most basic cellular activities in the body. See, Hastings, et al., "A Clockwork Web: Circadian Timing in Brain and Periphery, in Health and Disease," *Nature Reviews-Neuroscience* 4: 649-661 (2003). As might be expected, monitoring an individual's circadian cycles is useful in diagnosing and treating many conditions. See Turek, et al., supra; see also, International Patent Application No. PCT/US2007/020425 (Zhang et al. 2008) (requiring an implanted device for physiological monitoring).

Along these lines, Fuller, et al. note that "neuronal circuits responsible for circadian rhythm genesis, thermal control, feeding, and autonomic function are located in the hypothalamus," and studies have shown that the hypothalamus is influenced by the vestibular nuclei. "Neurovestibular Modulation of Circadian and Homeostatic Regulation: Vestibulohypothalamic Connection?" *Proceedings of the National Academy of Sciences* 99:24 15723-15728. See also, Fuller and Fuller, "Genetic Evidence for a Neurovestibular Influence on the Mammalian Circadian Pacemaker," *Journal of Biological Rhythms* 21:177-184 (2006). With the body's master clock located within the SCN region of the hypothalamus, there exists a need for controlled monitoring and stimulation of the vestibular system for managing the circadian cycle of an individual in a therapeutic environment. A continued need also exists for a device directed to stimulating the SCN brain tissue and modulating the circadian clock. At least one study has suggested that light therapy could be helpful in this regard. U.S. Pat. No. 6,135,117 (Campbell et al. 2000).

Other regions of the brain also show a potential benefit from a device and associated method for controlled vestibular stimulation. Researchers have determined that the vestibular system provides a direct conduit to the fastigial nucleus, an area of the brain rich with possibilities for assisting in the prevention of cellular ischemia and excitotoxic brain injuries. See Zhou, et al., "Electrical Stimulation of Cerebellar Fastigial Nucleus Protects Rat Brain, in vitro, From Staurosporine-Induced Apoptosis," *Journal of Neurochemistry* 79(2): 328-338 (2001); Siebold, et al. "Fastigial Nucleus Activity During Different Frequencies and Orientations of Vertical Vestibular Stimulation in the Monkey" *Journal of Neurophysiology* 82: 34-41 (1999). Ongoing research has also determined that the vestibular system is connected to the brain's release of acetylcholine from the hippocampus. Horii, et al., "Effects of Vestibular Stimulation on Acetylcholine Release from Rat Hippocampus: An In Vivo Microdialysis Study," *Journal of Neurophysiology* 72:2 605-611 (1994). Similar results have shown the increased production of histamines via vestibular stimulation of the hypothalamus. Horii, et al., "Effect of Unilateral Vestibular Stimulation on Histamine Release from the Hypothalamus of Rats In Vivo," *Journal of Neurophysiology* 70:5 1822-1826 (1993).

Vestibular stimulation has also been linked to blood chemistry changes that can be of use in treating various disease states. First, an increased concentration of ascorbic acid in the human body has been shown to result from cold water vestibular stimulation. See, Zhang, et al., "Change of Extracellular Ascorbic Acid in the Brain Cortex Following Ice Water Vestibular Stimulation: An On-line Electrochemical Detection Coupled with In-vivo Microdialysis Sampling," *Chinese Medical Journal* 121:12:1120-1125 (2008). Research also suggests that the inner ear is a logical place to stimulate heat shock protein formation for protection against acoustic overexposure. Sugahara, et al., "Heat Shock Transcription Factor HSF1 is Required for Survival of Sensory Hair Cells Acoustic Overexposure," *Hearing Research* 182: 88-96 (2003). Vestibular stimulation is one way to induce the heat shock protein response.

Yet another area of development involves the association between vestibular stimulation and the insula region of an individual's brain, which is critical in an individual's sensory system (particularly auditory), motor association, and vestibular activity. Bamiou et al., "The insula (Island of Reil) and its role in Auditory Processing," *Brain Research Reviews* 42:143-154 (2003). The insula is particularly reactive to thermal stimulation. See, Craig et al., "Thermosensory Activation of Insular Cortex," Nature Neuroscience 3:2: 184-190 (2000). The insula, therefore, is a prime area for researching the effects of caloric vestibular stimulation. This is particularly true for research and therapies that use holistic approaches to wellness, including meditation as a means for achieving clinical results in physiology and psychology. Research has shown a correlation between successful meditation and insular activity. Lutz et al., "Regulation of the Neural Circuitry of Emotion by Compassion Meditation: Effects of Meditative Expertise," *Public Library of Science—PLoS One* 3:3:1-10 (2008). Given the insular response noted upon the exposure of a body to thermal stimulus, the insula has significant potential in the area of hot flash management and other rapid changes in body temperature.

Accordingly, developments in stimulating the vestibular system of an individual are potentially beneficial to take full advantage of physiological responses that are useful in treating and diagnosing a variety of medical conditions. These conditions include but are not limited to Alzheimer's Disease, diabetes, obesity, heart disease, epilepsy, vertigo, hypercusis, fibromyalgia, menopause, phantom limb pain, migraine and numerous conditions for which the prescribed medicines work optimally at a particular point in a circadian cycle.

SUMMARY OF THE INVENTION

The present invention provides an in-ear device for delivering caloric and electrical vestibular stimulation to an individual, as well as other forms of therapy via the vestibular system. In one embodiment, the device comprises: (a) an ear insert so dimensioned as to be insertable into the ear canal of a wearer, the insert having an inner portion, (b) at least one thermoelectric transducer mounted on the ear insert inner portion; and (c) a sleeve or sheath connected to the ear insert inner portion and overlying the at least one thermoelectric transducer, through which sleeve heat can be conducted between each of said at least one thermoelectric transducers and the ear canal to deliver caloric vestibular stimulation to the wearer. The device is fully functional with or without the sleeve, as the thermoelectric transducers may be in direct contact with the ear canal.

Thus in some embodiments, the present invention provides an in-ear device for delivering caloric vestibular stimulation to an individual, comprising: (a) an ear insert so dimensioned as to be insertable into the ear canal of a wearer, the insert having an inner portion, the inner portion having a length dimension at least as great as a major portion of the length dimension of the ear canal of the wearer; (b) at least one thermoelectric transducer mounted on the ear insert inner portion; and (c) a sleeve-connected to the ear insert inner portion and overlying the at least one thermoelectric transducer, the sleeve comprising an elastic material, with the sleeve having an inner surface portion configured to conformably engage the ear insert inner portion and an outer surface portion configured to conformably engage the ear canal, so that heat can be conducted between each of the at least one thermoelectric transducers and the ear canal through the sleeve to deliver caloric vestibular stimulation to the wearer. In some embodiments the ear insert inner portion has a shape that corresponds to the ear canal of the wearer; in some embodiments the sleeve outer surface portion has a shape that corresponds to the ear canal of the wearer. In some embodiments the sleeve is removably connected to the ear insert inner portion. In some embodiments the ear insert includes an identifier associated therewith for indicating whether the ear insert is configured for insertion into a left or right ear canal. In some embodiments, the sleeve includes an identifier associated therewith for indicating whether the sleeve is configured for: (i) insertion into a left or right ear canal, or (ii) engagement on the ear insert inner portion when the ear insert is configured for insertion into a left or right ear canal. In some embodiments, the ear insert has an outer portion, the outer portion configured to overlie at least a portion of the external ear of a wearer. In some embodiments, the ear insert is configured to be positioned completely within the ear canal of the wearer. In some embodiments, the at least one thermoelectric transducer comprises at least two separately controllable thermoelectric transducers spaced apart from one another on the ear insert inner portion. In some embodiments, the ear insert further comprises an external transducer operatively associated therewith and configured for positioning on or adjacent the mastoid process of the wearer for delivering thermal, electric or mechanical stimuli to the wearer. In some embodiments, the ear insert has a canal formed therein to facilitate ventilation of the ear. In some embodiments, the ear insert further comprising an acoustic transducer operatively associated therewith for delivering auditory stimuli to the wearer.

In other embodiments, the present invention provides an in-ear device for delivering caloric vestibular stimulation to an individual, comprising: (a) a preformed ear insert so dimensioned as to be insertable into the ear canal of a wearer, the insert having an inner portion, the inner portion having a length dimension at least as great as a major portion of the length dimension of the ear canal of the wearer; and (b) at least one thermoelectric transducer mounted on the ear insert inner portion; the preformed ear insert having a surface portion configured to conformably engage the ear canal, so that heat can be conducted between each of the at least one thermoelectric transducers and the ear canal through the sleeve to deliver caloric vestibular stimulation to the wearer. In some embodiments, the ear insert has an outer portion, the outer portion configured to overlie at least a portion of the external ear of a wearer. In some embodiments, the ear insert configured to be positioned completely within the ear canal of the wearer. In some embodiments, the at least one thermoelectric transducer comprises at least two separately controllable thermoelectric transducers spaced apart from one another on the ear insert inner portion. In some embodiments, the ear insert is formed of a compressible material. In some embodiments, the ear insert further comprises an external transducer operatively associated therewith and configured for positioning on or adjacent the mastoid process of the wearer for delivering thermal, electric or mechanical stimuli to the wearer. In some embodiments, the ear insert has a canal formed therein to facilitate ventilation of the ear; and in some embodiments the ear insert further comprises an acoustic transducer operatively associated therewith for delivering auditory stimuli to the wearer.

A further aspect of the invention is a method of delivering caloric vestibular stimulation to an individual, comprising: (i) positioning a device as described herein within the ear canal (left or right, or both) of an individual, and then; (ii) activating the at least one thermoelectric transducer for a time and to a temperature sufficient to deliver caloric vestibular stimulation to the wearer (e.g., by heating or cooling the at least one transducer). In some embodiments, where the at least one thermoelectric transducer comprises at least two separately controllable thermoelectric transducers spaced apart from one another on the ear insert inner portion, and wherein the activating step comprises separately and selectively activating the at least two separately controllable thermoelectric transducers.

In a preferred embodiment, the in-ear device controls the circadian temperature cycle of an individual by providing a stimulus through the individual's ear. In this embodiment, the invention includes the above-reference features either alone or in combination, along with a timing element and a temperature element. The device further includes a computerized control module in electronic communication with the ear insert, the temperature element, and the transducer for controlling caloric vestibular stimulation according to data based on the individual's circadian temperature cycle.

The device may also include an electrode attached to the ear insert for providing electrical stimulation to the individual's vestibular system. In combination with the caloric vestibular stimulation, the electrical stimulation allows for vestibular stimulation to the individual's brain sufficient to produced desirable changes in blood chemistry and/or brain chemistry. In particular, the vestibular stimulation according to this invention promotes the production of bio-chemicals including but not limited to ascorbic acid, serotonin, heat shock proteins, acetylcholine, and histamines.

The present invention is explained in further detail in the drawings herein and the specification set forth below. All United States patent references cited herein are to be incorporated by reference herein in their entirety.

DETAILED DESCRIPTION OF THE PREFERRED EMBODIMENTS

The device and method of this invention utilize the vestibular system to induce physiological and/or psychological responses in an individual for medically diagnostic and therapeutic purposes. The terms "individual" and "wearer" in this document include but are not limited to humans who wear the device or perform the method of this invention. In other embodiments, an individual could refer to animals used in testing the device, animals receiving medical attention, or animals being used for medical research. Veterinarian purposes are within the scope of the disclosure herein.

The term "vestibular system" has the meaning ascribed to it in the medical arts, and includes but is not limited to those portions of the inner ear known as the vestibular apparatus and the vestibulocochlear nerve. The vestibular system, therefore, further includes, but is not limited to, those parts of the brain that process signals from the vestibulocochlear nerve.

Figure 1:
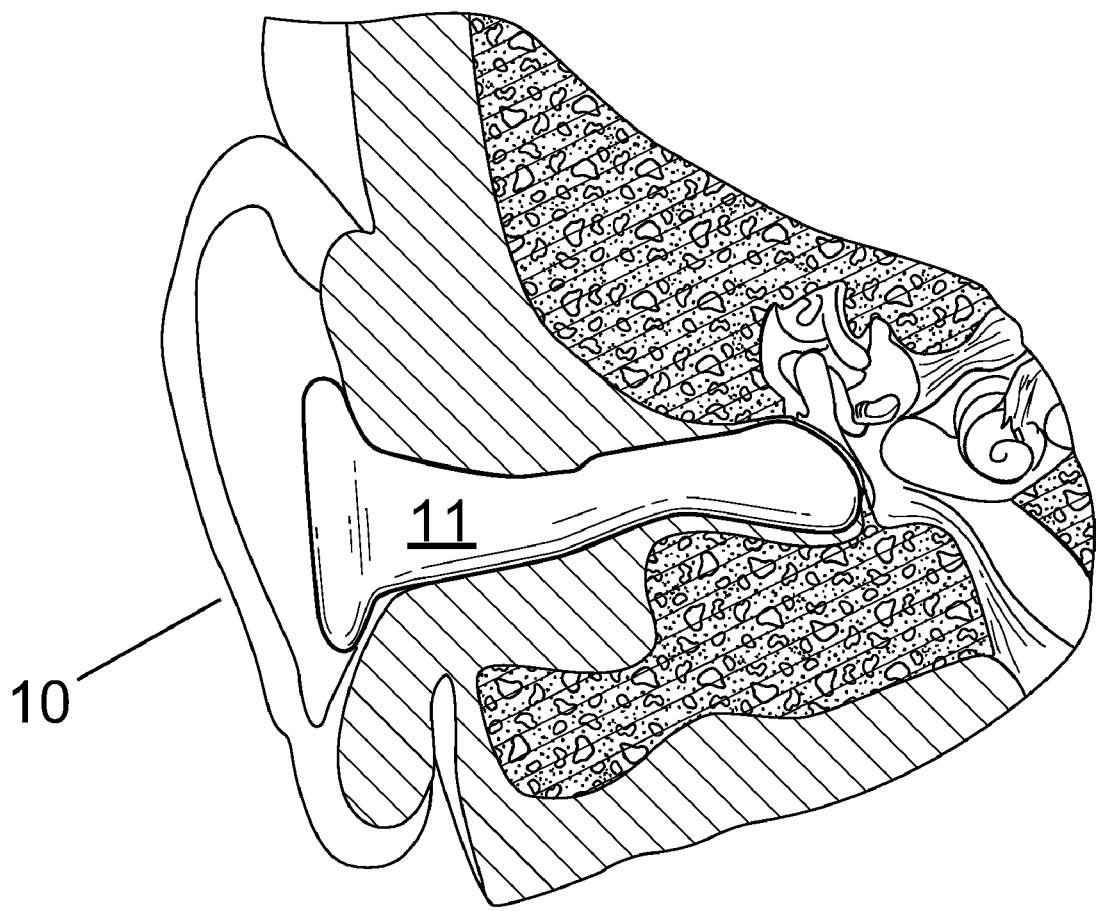
FIG. 1 illustrates a device of the invention inserted in the ear of a human wearer (the anatomical portion of the Figure is adapted from FIG. 2 of Grams et al., U.S. Pat. No. 4,244,377).
Figure 2:
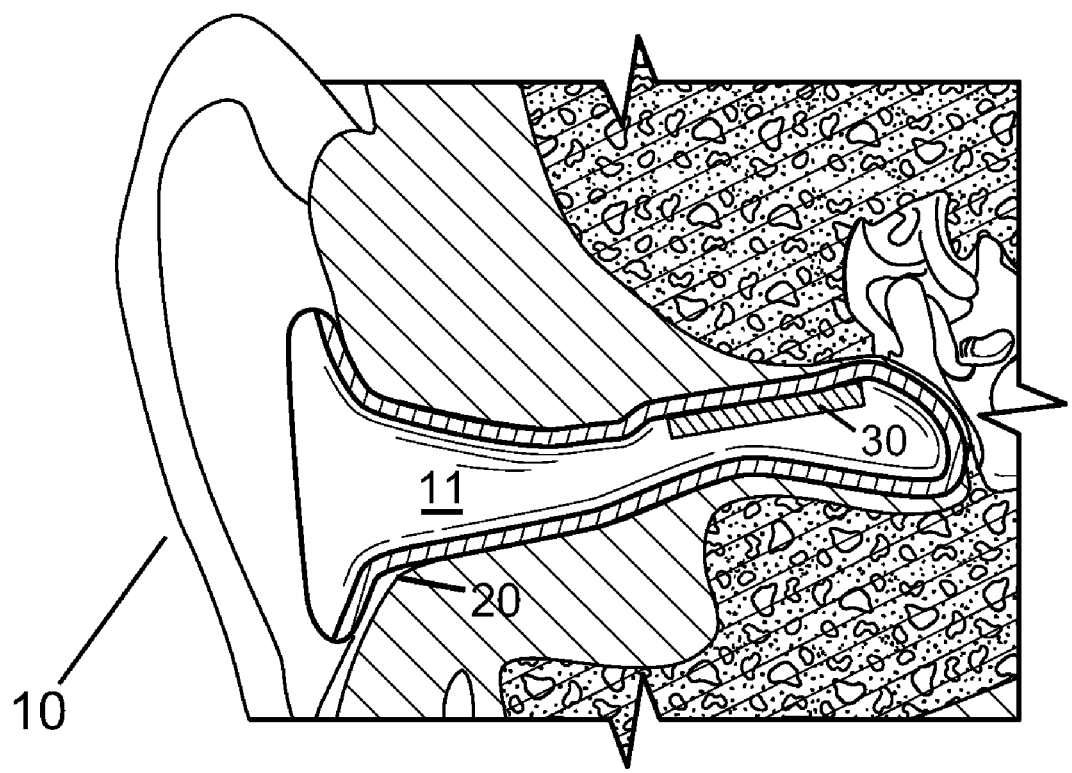
FIG. 2 is a further side-section illustration of the device of FIG. 1.

A first embodiment of a device 10 of the present invention inserted in the ear of a human wearer is schematically illustrated in FIGS. 1-2 (the anatomical portion of the figures is adapted from FIG. 2 of Grams et al., U.S. Pat. No. 4,244,377). As noted above, in one embodiment, the device 10 is an in-ear device for delivering vestibular stimulation to a human wearer. The device comprises an ear insert 11 so dimensioned as to be insertable into the ear canal 20 of a wearer. The ear insert has an inner portion 12, with the inner portion preferably having a length dimension at least as great as a major portion of the length dimension of the ear canal of the wearer (e.g., a length at least 50, 60, 70, or 80 percent that of the length dimension of the ear canal of the wearer).

The device disclosed herein incorporates active elements onto the ear insert 11 for engaging the ear canal 20 and thereby accessing the individual's vestibular system. For purposes herein, and without limiting the invention, the term "active elements" means those portions, regions, or components of the vestibular stimulation device 10 that induce a change in the ear canal 20 of the wearer. The change can be any physiological, structural, or physical response in the ear canal 20 capable of affecting the vestibular system of the individual. The term active elements includes, but is not limited to, temperature elements such as thermometers, thermoelectric transducers, electrodes, and other components useful in controlling the vestibular system.

As shown in FIG. 2 at least one thermoelectric transducer 30 is mounted on the ear insert inner portion 12. Any suitable thermoelectric device or transducer can be used to carry out the present invention, including but not limited to those described in U.S. Pat. Nos. 7,205,675; 7,098,393; 7,024,865; and 5,974,806; and in US Patent Application Publication No. 2004/0199266. See also S. Riffat and X. Ma, Thermoelectrics: A review of present and potential applications, *Applied Thermal Engineering* 23, 913-935 (2003). The transducer can be an electrothermal textile transducer, including but not limited to those described in U.S. Pat. Nos. 7,202,443; 6,977,360; and 6,229,123. The transducer is typically provided with a lead 31 which may be connected to an external power supply 35 and controller 38, or the power supply and controller may be contained within the device as discussed further below. This device disclosed herein further includes embodiments of thermoelectric transducers in all shapes and sizes, including but not limited to spiral and helical shapes.

In some embodiments, a plurality of thermoelectric transducers may be mounted on an elongated flexible strip by any suitable technique, including but not limited to those described in Hiller et al., U.S. Pat. No. 7,147,739. In other embodiments, where it is desired to generate an electric current from the transducer, the transducer can be a mechanical or piezoelectric transducer. Examples include but are not limited to both piezoelectric devices and zinc-oxide nanowire nanogenerators. See, e.g., X. Wang, "Direct-Current Nanogenerator Driven by Ultrasonic Waves," *Science* 316: 102-105 (Apr. 6, 2007). Z. Wang, "Piezoelectric Nanogenterators Based on Zinc Oxide Nanowire Arrays," *Science* 312: 242-246 (Apr. 14, 2006); P. Patel-Predd, "Nanogenerator Fueled by Vibrations," *MIT Technology Review* (Apr. 5, 2007).

Thin film thermoelectric devices or transducers are preferred as transducers in some embodiments, including but not limited to the thin film thermoelectric devices described in U.S. Pat. No. 6,300,150 and US Patent Application Publication Nos. 2007/0028956 and 2006/0086118. Such thin film thermoelectric devices may also advantageously incorporate a temperature sensing function, so that temperature sensing can be accomplished through the same device without the need for a separate temperature sensor.

The ear insert 11 can be formed of any suitable material, including flexible materials (particularly where the ear insert is shaped in conformance with the ear canal of the subject) and rigid materials (e.g., when a more cushioning sleeve is utilized). The ear insert 11 can be formed by any suitable technique, such as molding or casting, with the thermoelectric device 30 or transducer (and any associated wires or leads) cast or molded in place in accordance with conventional techniques.

The ear insert 11 can in some embodiments have a canal formed therein to facilitate or permit natural ventilation of the ear, as described in U.S. Pat. No. 6,819,770 to Niederdrank. If desired for some embodiments, the ear insert 11 can also include an acoustic transducer for delivering auditory or sound stimuli to the wearer.

As shown in FIG. 2, a sleeve or sheath 40 may be connected to (e.g., removably connected to; permanently connected to; or formed on) the ear insert inner portion 12. As shown most clearly in FIG. 4, the sleeve may have a closed medial end portion 41 and an open outer end portion 42. In some embodiments, the sleeve 40 has an inner surface portion configured 45 to conformably engage the ear insert inner portion 12, and an outer surface portion 46 configured to conformably engage the ear canal 20 of the wearer, Hence, heat can be conducted between (that is, to or from) each of the at least one thermoelectric transducers 30 and the ear canal 20 through the sleeve 40 to deliver caloric vestibular stimulation to the wearer.

Figure 3:
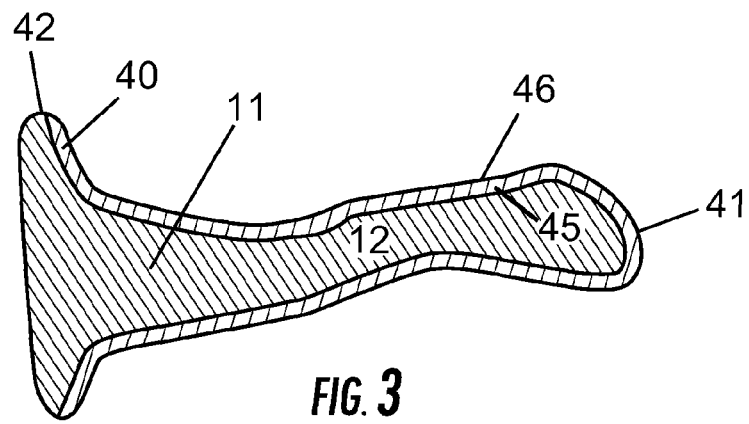
FIG. 3 is a side-section illustration of one embodiment of the invention, in which the ear insert inner portion has a shape that corresponds to the ear canal of the wearer.
Figure 4:
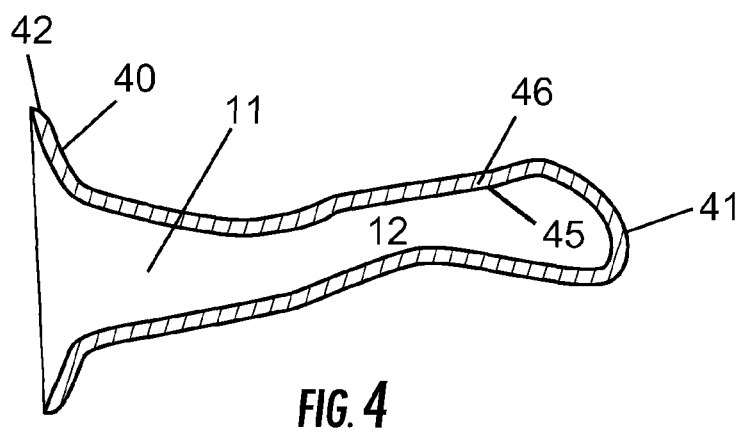
FIG. 4 is a side-section illustration of the sleeve of the device of FIG. 3 removed from the ear insert.
Figure 5:
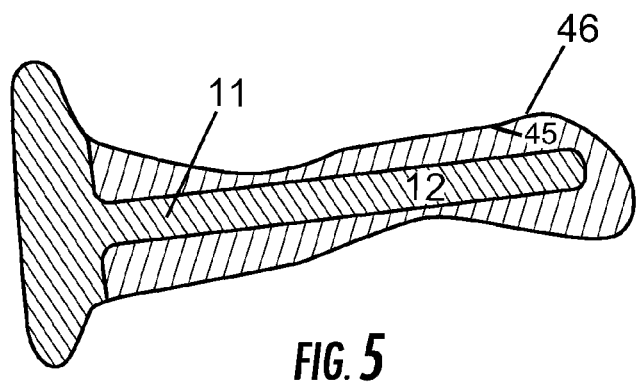
FIG. 5 is a side-section illustration of another embodiment of the invention, in which the sleeve outer portion has a shape that corresponds to the ear canal of the wearer.
Figure 6:
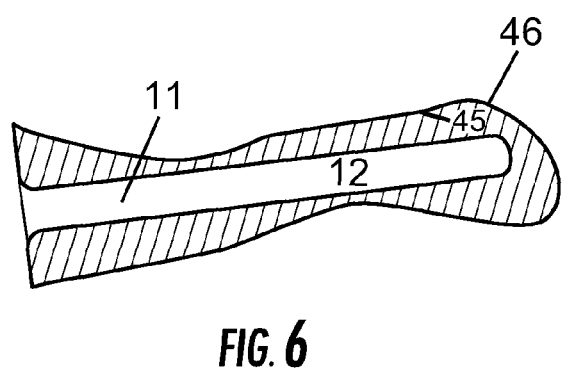
FIG. 6 is a side-section illustration of the sleeve of the device of FIG. 5 removed from the ear insert.

In some embodiments, such as shown in FIGS. 3-4, the ear insert inner portion 12 has a shape (i.e., a preformed shape) that corresponds to the ear canal 20 of the wearer. In such an embodiment the sleeve 40 is configured to correspond to the shape of the ear insert inner portion 12, but conforms to the ear canal 20 of the wearer only when mounted on the sleeve insert inner portion 12. In other embodiments, such as shown in FIGS. 5-6, the ear insert inner portion 12 does not have a shape that corresponds to the shape of the ear canal 20 of the wearer, but the sleeve outer surface portion 46 instead has a shape (i.e., a preformed shape), that corresponds to the ear canal of the wearer. Both embodiments provide, when assembled, a sleeve inner surface portion 45 that conformably engages the ear insert inner portion 12, and an outer surface portion 46 that conformably engages the ear canal 20 of the wearer. Hence, in both embodiments heat can be conducted between each of the at least one thermoelectric transducers 30 and the ear canal 20 through the sleeve 40, as discussed above.

The sleeve 40 can comprise, consist of, or consist essentially of any suitable elastic and/or compressible material, such as a polymer, a textile (woven or non-woven) or a composite thereof. In some embodiments the polymer comprises a hydrogel polymer, a thermally conductive resin, and/or a viscoelastic polymer (it being understood that some but not all viscoelstic polymers will be hydrogel polymers; and some but not all hydrogel polymers will be viscoelastic polymers). Numerous suitable hydrogel polymers, including biodegradable or bioerodable hydrogel polymers, and stable hydrogel polymers (e.g., silicone hydrogel polymers) are known. Examples include but are not limited to those described in U.S. Pat. Nos. 7,213,918; 7,171,276; 7,105,588; 7,070,809; 7,060,051; and 6,960,625. Suitable viscoelastic polymers include but are not limited to those described in, for example, U.S. Pat. Nos. 7,217,203; 7,208,531; and 7,191,483. An ester-based viscoelastic memory foam such as used in the heating pad systems described in U.S. Pat. No. 7,176,419 is among those suitable for use in making sleeves of the present invention. In some embodiments, the sleeve 40 has a thermal conductivity of from 0.1 to 50 W/m×K; and a hardness of from 0 to 50 on the Shore A scale.

The sleeve 40 can be made by any suitable technique such as molding, casting, etc. While in some preferred embodiments the sleeve 40 is removable, in other embodiments that sleeve is formed on, integrally formed with, or otherwise permanently connected to the ear insert 11. The sleeve 40 can be open at both the medial 41 (closest to the ear drum) and outer ends 42 thereof, or open at the outer end 42 only. When the ear insert 11 has a canal formed therein to facilitate ventilation of the ear, the sleeve 40 is preferably open at both the proximal and distal ends of the canal. The sleeve 40 may be transparent or tinted with a pigment, in whole or in part such as in one or more defined locations on the sleeve (e.g., the medial portion, the outer portion, the upper portion, the lower portion, the front portion, the back portion) to provide an indicator of whether the sleeve is for a left or right ear canal device, an indicator of size of the sleeve, an indicator of how the sleeve should be oriented on the insert, etc.

Devices of the present invention can be used singly or in pairs. The ear insert 11 can optionally include an identifier associated therewith for indicating whether said ear insert is configured for insertion into a left or right ear canal. Likewise, the sleeve 40 can optionally include an identifier associated therewith for indicating whether said sleeve 40 is configured for: (i) insertion into a left or right ear canal, or (ii) engagement on said ear insert inner portion when said ear insert is configured for insertion into a left or right ear canal. Such identifiers can be printed, stamped, or molded symbols such as "L" for left and "R" for right; color coding for left and right; etc.

In FIGS. 1, 2, 3 and 5 the ear insert 11 has an outer portion 13, the outer portion 13 configured to overlie at least a portion (e.g., some or all) of the external ear 22 of a wearer. This creates an external appearance, when worn, similar to that of a half-shell or full-shell hearing aid. However, any suitable configuration can be utilized, as further shown in FIGS. 9-10, in which the device is configured to be positioned in the canal or completely in the canal of the wearer. Note also in FIG. 10 that the device medial portion 14 does not abut the eardrum, as would the medial portion 14 of the device of FIG. 9.

Figure 7:
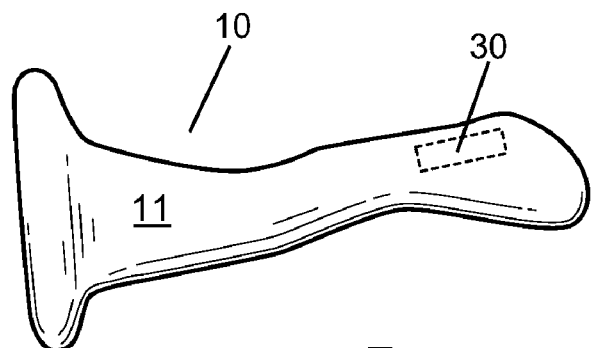
FIGS. 7-10 illustrate various alternate embodiments of the invention, of different length dimension, and with different transducer arrangements.
Figure 8:
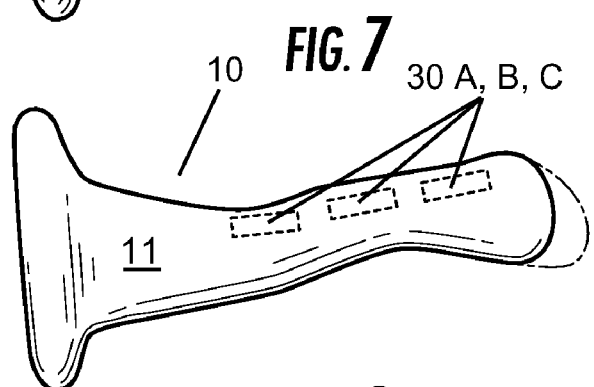
Figure 9:
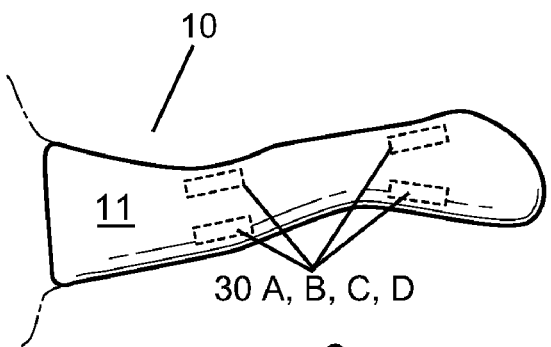
Figure 10:
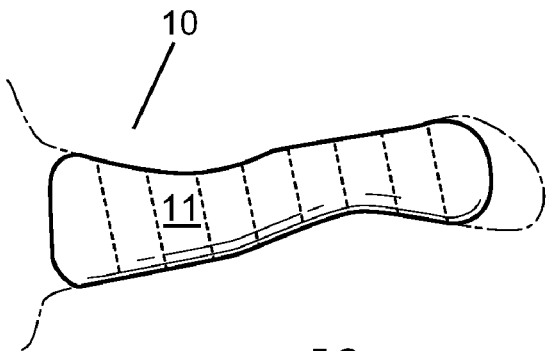
Figure 11:
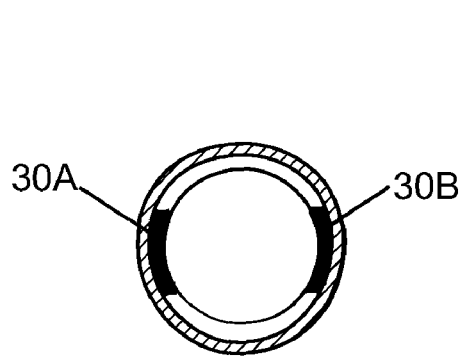
FIGS. 11-12 are cross-sectional illustrations of embodiments of the present invention, showing different transducer arrangements.
Figure 12:
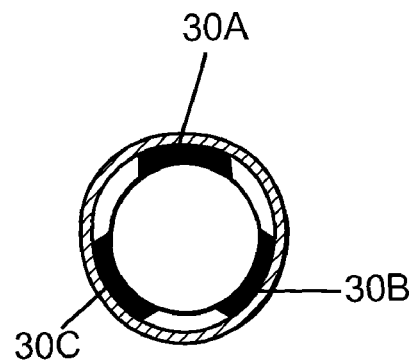

FIGS. 7-12 illustrate various transducer arrangements in devices of the present invention. While a single thermoelectric transducer 30 can be used, in some embodiments it is preferable to include at least two, three, or four (or more) separately controllable thermoelectric transducers 30a, 30b, 30c, 30d, which can be spaced apart from one another on the ear insert inner portion 12. As shown in FIGS. 7-9, the transducers can be positioned longitudinally along the insert 11; as shown in FIG. 10, the transducers 30 can be positioned laterally along the insert 11. Other positionings, such as angled positionings, and combinations of the foregoing, can also be used. Further, while the transducers are depicted as rectangular in shape, any suitable regular or irregular shape can be used.

Figure 13:
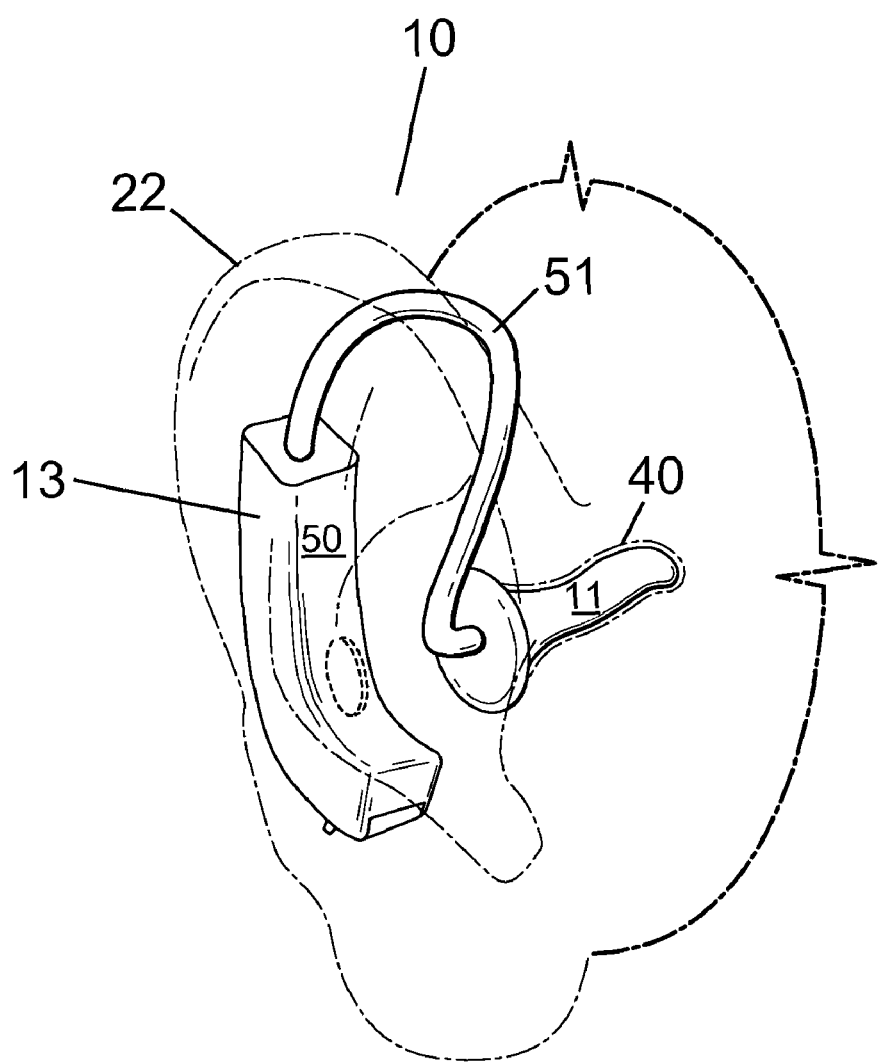
FIG. 13 illustrates an embodiment of the present invention that includes an external body portion configured for positioning behind the ear of a wearer.
Figure 14:
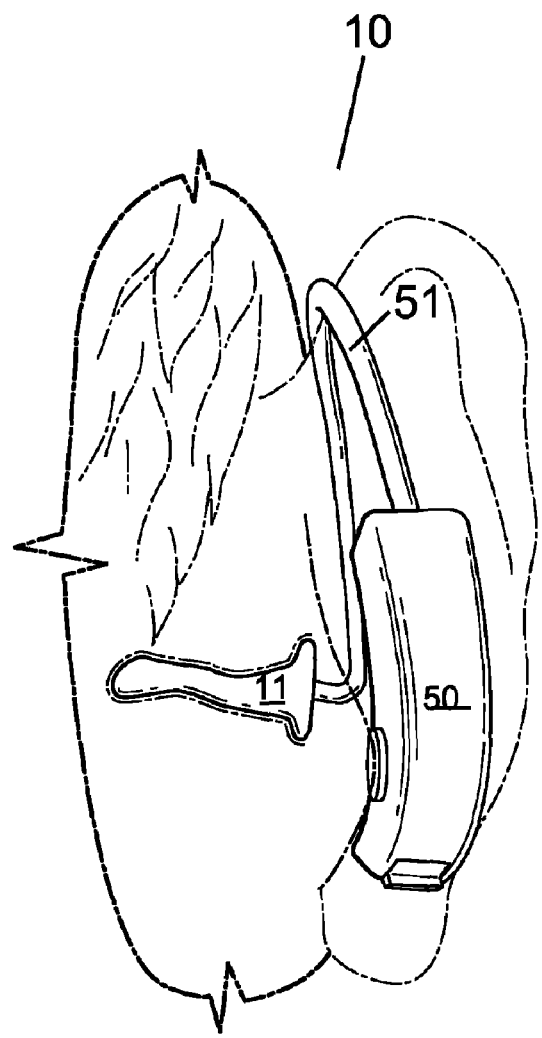
FIG. 14 is a further illustration of the embodiment of FIG. 13 from behind the wearer, showing the additional external transducer positioned on or adjacent the mastoid process of the wearer.

FIGS. 13-14 illustrate a further embodiment of the present invention, in which an external housing 50 is connected to the ear insert by a bridge member 51 (here, in the shape of a tube). The external housing 50 is configured for positioning behind the ear of a wearer. The housing 50 can contain a computerized control module, control circuitry, a power supply such as a battery, controls such as an on-off switch 52, etc. In the illustrated embodiment the housing has an external transducer 53 mounted on the medial surface 54 thereof, which external transducer can deliver thermal, electric, or mechanical stimuli to the wearer at subthreshhold (e.g. stochastic) or superthreshhold levels, which stimuli may be given in any suitable pattern alone or in cooperation with stimuli from the ear canal transducers. Note that the external transducer can be positioned on the housing so that it contacts the wearer on or adjacent to the mastoid process 25 of the wearer.

Figure 15:
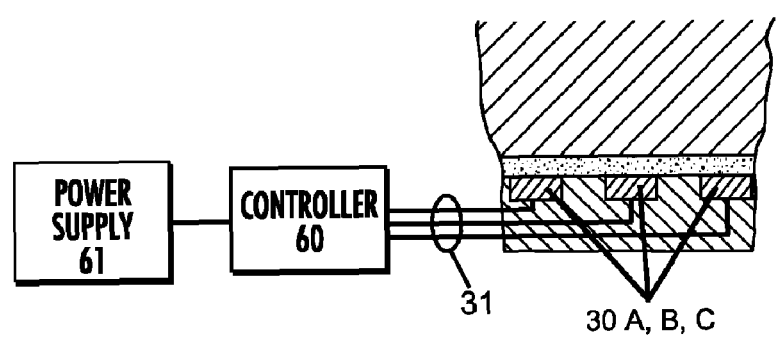
FIG. 15 is a schematic illustration of an apparatus of the invention operatively associated with a power supply and controller.

FIG. 15 schematically illustrates a device of the present invention operatively associated with a controller 60, which controller is in turn operatively associated with a power supply 61. The controller and power supply can be contained within the device (e.g., in an external housing as described in connection with FIGS. 13-14 above), in a belt-worn or other housing, connected to a stationary unit such as a personal computer, or in any other suitable configuration. In a preferred embodiment, the controller includes a computerized control module 70 programmed with computer instructions (i.e., software) that controls the magnitude, duration, wave pattern, and other attributes of the vestibular stimulation.

As shown in FIG. 15, once the device is positioned within the ear canal 20 of a subject or wearer, the at least one thermoelectric transducer 30a, 30b, 30c, each of which is operatively associated with the controller by a separate lead 31a, 31b, 31c, is activated for a time and to a temperature sufficient to deliver caloric vestibular stimulation to the wearer. An adjustable or programmable control module 70 can be utilized to optimize stimulation for a particular wearer, and for a particular purpose or condition. Where (as shown in FIG. 15) there are at least two separately controllable thermoelectric transducers on the ear insert inner portion spaced apart from one another, the activating step can comprise separately and selectively activating the at least two separately controllable thermoelectric transducers (e.g., by activating only one or two thereof, by heating one transducer and cooling another; by sequentially activating transducers; by activating different transducers to different degrees; combinations of some or all of the foregoing, etc.) Patterns of separate and selective activation can be preprogrammed, can be determined empirically, can be optimized by the wearer or a programmer (such as a clinician) in a programming session with the wearer, etc.

The control module can be part of a multimodal stimulation system for creating a "virtual environment" for the wearer, such as described in U.S. Pat. No. 5,762,612 to Campbell. If desired, the device can incorporate sensors or monitoring probes for positioning in the ear canal, such as described in Fischer et al., US Patent Application Publication No. 2007/0112277 (May 17, 2007) and in J. Fraden, US Patent Application Publication No. 2005/0209516 (Sep. 22, 2005).

Subjects or wearers for the devices of the present invention are often, but are not limited to, human subjects, including both male and female subjects at any stage of development (e.g., juvenile, adolescent, adult, and geriatric subjects). While the shape of ears and ear canals 20 thus will vary among subjects or wearers, and different sizes and combinations of ear inserts and sleeves will likely be necessary to accommodate different wearers, an optimal set of inserts and sleeves can be developed through the use of statistical shape analysis (see, e.g., R. Paulsen, Statistical Shape Analysis of the Human Ear Canal with Application to In-the-Ear Hearing Aid Design (Kongens Lyngby 2004) to provide ready availability of the devices of the present invention without the need to custom mold a device for each individual wearer, particularly through the added adaptability between subjects contributed by the compressible sleeve 40 portion.

In some embodiments, an insert 11 of the invention is preformed to conform to, and hence conformably engage, the ear canal 20 of a particular wearer. Such a preformed insert 11 can be produced by forming an ear impression, which ear impression can then be used for casting in analogous manner as described in U.S. Pat. No. 6,249,587, or can instead be scanned and utilized for subsequent casting, three-dimensional ink jet printing, and/or other three dimensional construction (via deposition or removal of materials), as described in U.S. Pat. Nos. 7,162,323; and 6,986,739 (see also S. Fuller, "Ink-jet printed nanoparticle microelectromechanical systems", *Journal of Microelectromechanical Systems* 11, 54-60 (2002). With such a preformed device the need for a sleeve may be obviated, although it is preferred that the ear insert itself comprise or be formed of a soft resilient material (e.g., having a hardness of from 0 to 50 on the Shore A scale).

The present invention is useful for a variety of different purposes. The device can be used to enhance spatial and verbal memory function, as described in D. Bachtold et al., supra. The device can be used, individually or in pairs, to augment or control a patient's respiratory function, induce sleep, and/or counteract dizziness or vertigo, as described in U.S. Pat. No. 6,748,275 to Lattner. The device can be used to treat neurological disorders, headache (including migraine headache), seasickness and travel sicknesses, as described in O. Kolev, supra, and US Patent Application Publication No. 2003/0195588 to Fischell et al. The device can be used to improve or enhance autonomic and/or motor responsiveness in patients afflicted with central neurodegenerative disorders such as Parkinson's disease, as described in Y. Yamamoto et al., supra. The device can be utilized to treat pain such as thalamic pain syndrome, as described in V. Ramachandran et al., supra. The device can be utilized in a "virtual environment" educational, entertainment or training system, such as described in U.S. Pat. No. 5,762,612 to Campbell.

The device 10 of this invention is useful for diagnostic purposes. Instead of using the previously noted water caloric tests to determine levels of consciousness, the in-ear device disclosed herein is more efficient, avoids water spills, and provides adjustable ranges of stimulation. Levels of consciousness are not the only diagnostic measures possible with the device 10. A health care worker using the device of this invention would also be equipped to combine vestibular stimulation with brain scans to determine which areas of the brain are actively engaged at any given time. By comparing a healthy brain exposed to vestibular stimulation with a patient's brain scan during vestibular stimulation, the medical professional would quickly notice areas showing different levels of activity. The differences could be crucial in identifying regions of the patient's brain that are in a diseased state. Such information allows for more accurate diagnoses and more rapid medical intervention.

One other area of particular interest for the method and device of this invention lies in diagnosing and treating phantom limb pain. Phantom limb pain is a condition in which a patient experiences ongoing sensations that an amputated or missing limb is still present. The sensations often present as pain. Modern research indicates that the region of the brain associated with phantom limb pain is the thalamus. Brown, C. J., "Phantom of the Thalamus," *Canadian Medical Association Journal* 158:711 (1998).

As noted in the Background portion above, the device 10 described herein is useful for tracking, monitoring, and adjusting an individual's circadian rhythms. It is well known that body temperature fluctuates in a circadian cycle. In one embodiment, therefore, the device 10 controls the circadian temperature cycle of an individual by providing a stimulus through the individual's ear. The device according to this embodiment includes an ear insert that is shaped similarly to and engages the individual's ear canal. A temperature element attached to the insert measures changes in the individual's body temperature over time, preferably during a non-diseased state. In accordance with this embodiment, the system of this invention tracks the temperature readings over a time period of at least 24 hours and records the measurements as a data set. These measurements are useful in establishing a baseline temperature circadian cycle that is unique for that individual.

The ear insert 11 further includes at least one thermoelectric transducer 30 attached to the insert 11 for providing caloric vestibular stimulation to the individual. The thermoelectric transducer 30 may be contained entirely within the insert 11 or may be attached to the separate sleeve 40 described above. The thermoelectric transducer 30 used in the device 10 may be a thermoelectric cooler common in the industry today. The thermoelectric transducer 30 is capable of providing caloric stimulation to the individual's inner ear by allowing for the transfer of heat to and from the ear canal 20, thereby raising and lowering the temperature of the ear canal 20 as desired. The ear canal serves as a useful conduit to the individual's vestibular system.

The above-noted temperature 75 element measures the body temperature of the individual wearing a device. The temperature element 75 allows for monitoring the circadian temperature cycle for that individual. In a preferred embodiment, the monitoring function is accomplished by a computerized control module 70 in electronic communication with the insert, the temperature element 75, and the transducer 30. The control module 70 includes instructions, or computer commands, stored thereon for adjusting the rate of heat transfer between the transducer and individual's ear canal. The rate adjustment occurs in response to signals from the control module 70. The control module 70 may be located in the above-described outer portion 13 of the overall device 10; the outer portion 13 conveniently fits around the outer ear. In other embodiments, the control module 70 may be included in or combined with any peripheral device that is capable of achieving a therapeutic result (i.e., the control module 70 may be housed in a personal computer or other medical device as part of an overall medical system).

The temperature element 75 signals transmitted back to the control module 70 may be utilized in real time for immediately adjusting the output from the control module 70. Alternatively, in a different embodiment, the control module 70 may store historical body temperature data to establish a circadian temperature cycle over a known period of time. In the latter embodiment, the control module 70 may be programmed to regulate the vestibular stimulation directed to an individual at a particular point in the circadian cycle some time in the future. Whether real-time vestibular stimulation or programmed, delayed start stimulation is used, the device 10 and system according to this invention function to provide caloric stimulation to an individual's vestibular system, thereby raising and lowering the temperature of the ear canal. The control module 70 can be programmed to apply vestibular stimulation according to previously set instructions and functions such as ramping functions, square wave functions, and other mathematical algorithms.

For embodiments of the device 10 used to control an individual's circadian cycle, the device incorporates a time-keeping element, which may be a simple clock 80. The clock 80 is also in electronic communication with the computerized control module 70, as well as other components that are part of the overall vestibular stimulation system. The clock 80 of this device 10 allows the user to program the control module 70 in a way that tracks an individual's physiological data in the time domain, thereby allowing for planned therapeutic intervention at a certain time, including the present. The device 10 includes a mechanism for adjusting the time on the clock 80 to account for natural time changes such as daylight savings time and crossing time zones during travel. The mechanism for adjusting the time may be simple directional arrows for up and down time changes or more sophisticated electronics useful in the art of time keeping. In any event, the device 10 is equipped to maintain the current time in which an individual presently resides. In this way, the control module 70 can include instructions programmed into associated software that account for phase shifts in the individual's circadian cycle. The most common phase shift occurs in the time domain, and the control module, in conjunction with the associated clock, includes programs capable of providing vestibular stimulation in a way that synchronizes the individual's circadian cycle with the current time zone.

In a different embodiment, the device 10 is useful for alerting an individual or that individual's health care provider that the circadian cycle currently in place in the individual's body does not match the real geographical time (i.e. local time) that the individual is currently experiencing. In other words, the device described herein incorporates artificial intelligence sufficient to compare an individual's baseline circadian cycle, real-time circadian cycle, and current geographical time in a way that allows the individual to adjust medical interventions as appropriate.

As an example, certain medications work optimally at a particular point in an individual's circadian temperature cycle. When the individual is living according to a common routine, his or her health care provider can determine the time of day that the individual should take certain medications. If that individual's circadian cycle is shifted at any point due to significant changes in routine, the prescribed time of dosing may become inaccurate. The same is true when the individual crosses time zones during travel. The inner ear device described herein is capable of numerous interventions during any of these situations. First, the device 10 uses feedback from sensors (30, 75) engaging the ear canal 20 to alert the individual that the circadian cycle for a certain physiological parameter, such as temperature, has shifted, and the individual should shift the time for taking a certain medicine appropriately.

In a different embodiment, the health care provider may determine that circadian shifts away from the baseline are detrimental to the patient's well-being. In this case, the health care provider needs a way to re-set the patient's circadian clock to match geographical time. To achieve this result, the control module 70 within the device 10 may be programmed to provide vestibular stimulation in a way that actually moves and changes that individual's circadian cycle. As noted above, the most direct route to resetting the circadian cycle is through the SCN region of the brain, because the vestibular system is a direct conduit to the body's master clock in the SCN.

One goal of this invention, therefore, is to provide a mechanism and computerized method of stimulating an individual's brain by directing energy in the form of electrical current, heat transfer, light, pressure differentials, and other sources to the vestibular system. This energy is ultimately transferred through the vestibular system to the brain. By testing and optimizing physiological parameters, computer software instructions can be incorporated into the device 10 to direct the output from elements (30, 75) engaging the ear canal 20. For instance, without limiting the invention in any way, the computerized control module 70 directs heat output from a thermoelectric transducer 30 and/or electrical output from an electrode 85 at a magnitude and time duration that actually affects the brain chemistry, blood chemistry, and circadian cycle for that individual. For embodiments utilizing electrical vestibular stimulation, different patterns or waveforms may be used. These patterns include uniform pulse, random pulse, amplitude modulated pulses, and ramped pulses.

Regions of the brain that may be affected via vestibular stimulation include, but are not limited to, the SCN, the cerebellar fastigial nucleus, the insula cortex, and regions of the brain adjacent to these. By stimulating appropriate areas in the individual's brain via the vestibular system, the computerized control module 70 and the associated elements of the ear insert 11 can be programmed to induce biochemical and other physiological changes in the individual's body. Notably, the ear insert 11 can be programmed to induce serotonin output, ascorbic acid output, acetylcholine release, histamine release, and/or the production of heat shock proteins with therapeutic value.

Figure 16:
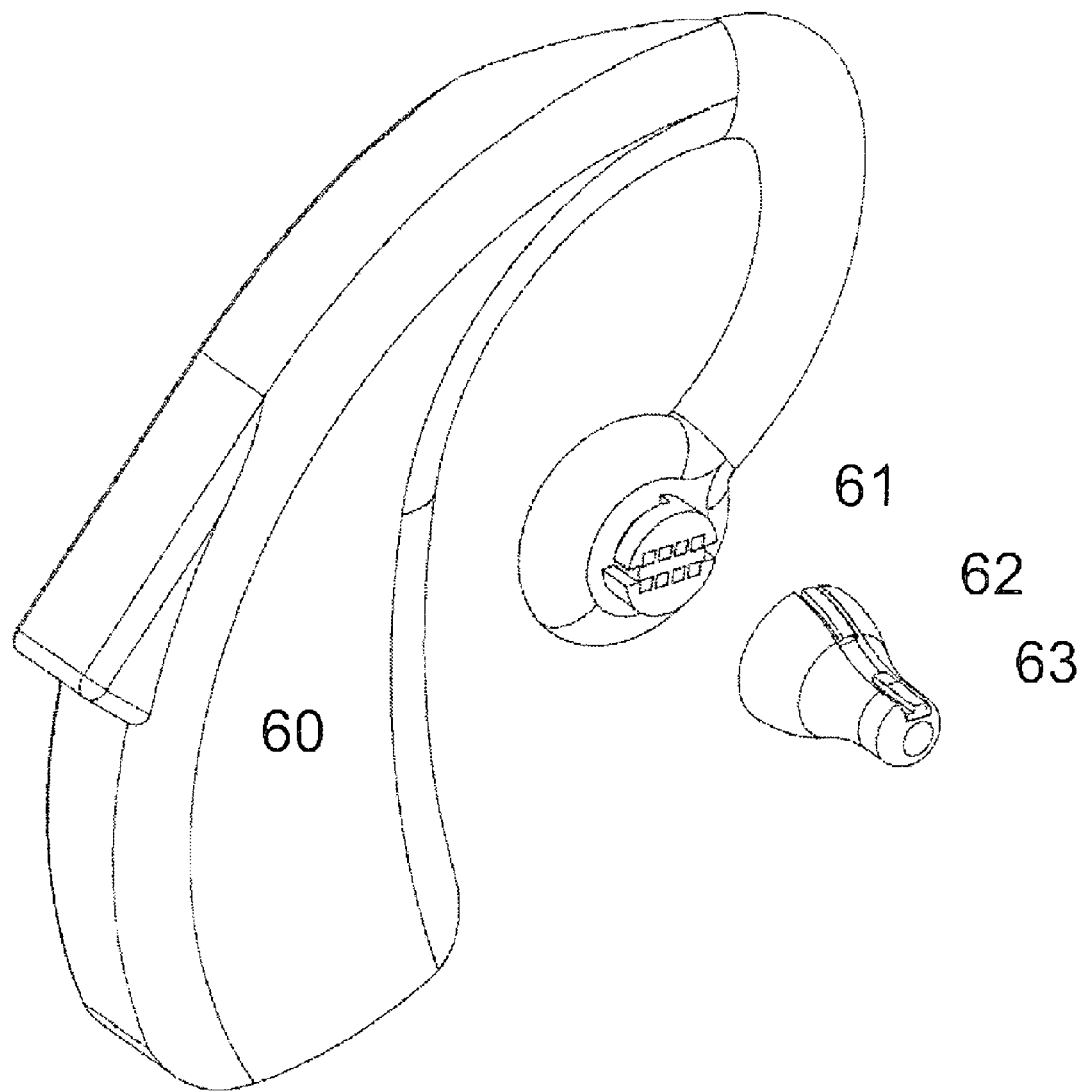
FIG. 16 is a schematic illustration of an apparatus in which the components therein are modular.
Figure 17:
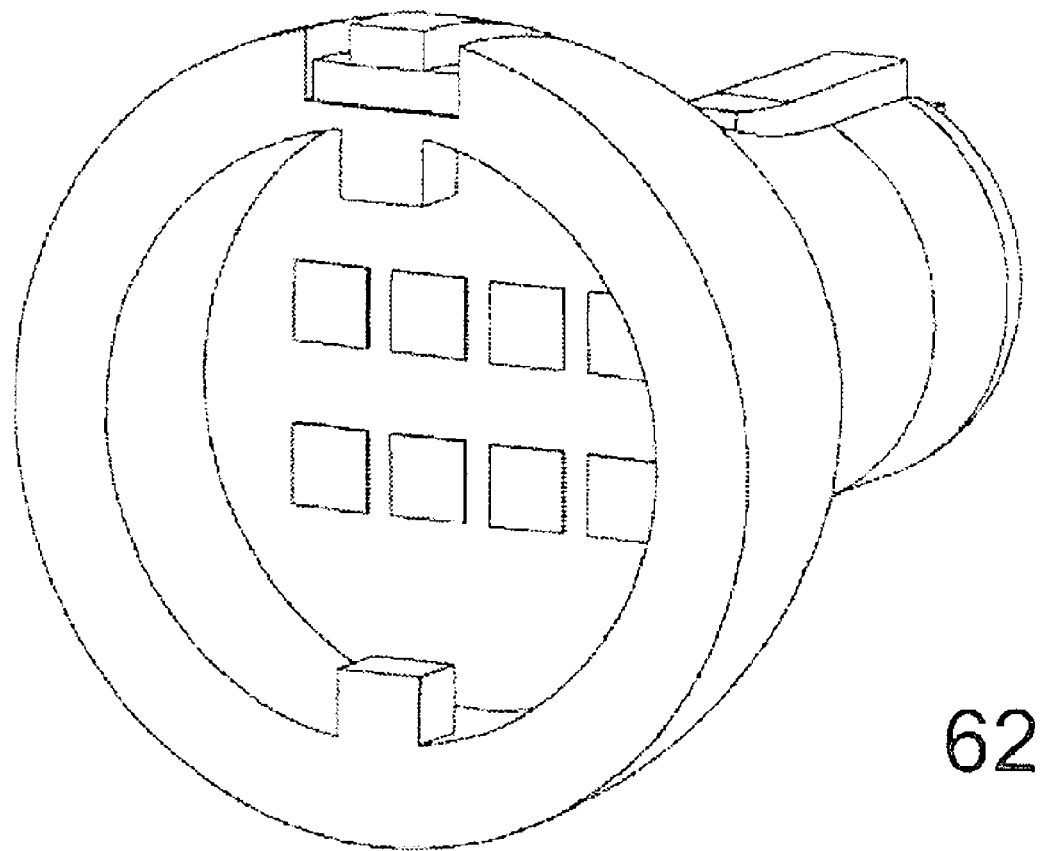
FIG. 17 is a schematic illustration of that portion of a modular insert engaging the ear canal.

A different embodiment of the vestibular stimulating device 10 is shown in FIGS. 16 and 17. In this embodiment, which is in no way limiting of the invention, the device includes the ear insert 11, thermoelectric transducer 30, electrode 85, and computerized control module 70 described above. As shown in FIGS. 16 and 17, however, the active elements (30, 70, 85) on the insert 11, including any transducer 63 or electrode 64, occupy adjustable positions for greater control over the device 10. The ability to adjust the position of the active elements on the insert allows for greater flexibility in directing stimulation in a way that is customized for that person. Minor changes in the direction and location of output can have large consequences for different individuals. As shown in FIGS. 16 and 17, one embodiment of the device includes modular portions 60-62 that fit together and come apart for greater variety in positioning the output. The modular structure shown in FIGS. 16 and 17 also allows for interchangeable ear inserts to be used with a single control module housed in the outer portion of the device.

Interchangeable ear inserts 62 are useful to allow for a variety of modifications in keeping with the scope of this invention. For example, a single individual might require therapy with fewer or greater numbers of any active element. As noted herein, the device 10 includes the flexibility to increase or reduce the number of electrodes 64, transducers 63, or other active elements necessary to achieve a desired result. Also, the modular nature of the device shown in FIGS. 16 and 17 allows for portions or pieces of the device 10 to be replaced without replacing the whole device. An ear insert 62 might be less expensive to replace than the computerized control module. Accordingly, FIGS. 16 and 17 illustrate schematically one embodiment of a modular vestibular stimulation device in which the active elements, located on either the ear insert 11 portion, or possibly a sleeve 40 as described above, are attached to an outer portion 50 via standard electrical connectors.

The vestibular stimulation device 10 is operational as an individualized piece of equipment worn by a single user, similar to the way a person wears a hearing aid. In different embodiments, however, the device 10 can be incorporated into a larger medical system. In one embodiment, the computerized control module 70 connects to peripheral equipment for added functionality. In a preferred embodiment, the device 10 is part of a larger therapeutic system that includes other devices for monitoring physiological parameters. Without limiting the types of peripheral equipment connecting to the device described herein, one useful peripheral sensor measures galvanic skin resistance. Skin resistance is a significant factor in estimating certain physiological and emotional changes that an individual is experiencing. When data tracking skin resistance are combined with data tracking a circadian cycle, such as the temperature cycle, the result is a broader, more holistic approach to treating an individual. Skin resistance also provides information regarding changes and phase shifts to the circadian cycle and is therefore useful as a feedback check on the effectiveness of any currently administered vestibular stimulation. Accordingly, in one aspect, the device 10, particularly the computerized control module 70, processes data gathered by peripheral devices, such as a galvanic skin resistance, and adjusts device 10 output accordingly.

In line with this galvanic skin resistance model, the device is useful for practicing a method of delivering vestibular stimulation to an individual's brain. In one embodiment, the method includes (i) arranging a thermal transducer 30 and an electrode 85 on an ear insert 11 in a position to stimulate the vestibular system of the wearer, (ii) electronically connecting the transducer 30 and the electrode 85 to a controller 38, and (iii) supplying the controller 38 with galvanic skin resistance data and temperature data from the individual. Next, the device 10 activates the transducer 30 and the electrode 85 via the controller 38. The transducer regulates heat exchange within the ear canal for a time and to a temperature sufficient to deliver vestibular stimulation to the individual. Similarly, the electrode 85 provides electrical stimulation to the vestibular system according to pre-set functions within the controller 38. In combination, the controller 38, the transducer 30, and the electrode 85 deliver vestibular stimulation, wherein the vestibular stimulation is selected from caloric stimulation, electrical stimulation, and combinations of each. The method further includes the step of measuring physiological changes in the individual, wherein the physiological changes are selected from the group consisting of brain chemistry changes and blood chemistry changes. The step of measuring physiological changes can be selected from the group consisting of circadian temperature cycle time shifts, ascorbic acid production, serotonin production, histamine production, acetylcholine production, and heat shock protein production.

The device 10 of this invention effectively provides vestibular stimulation, and therefore direct brain tissue stimulation, in numerous embodiments that include combinations and sub-combinations of the various elements described above. It is entirely within the scope of the device for the ear insert to be used with or without the above-described sleeve 40, which in one embodiment is removable and disposable. Similarly, the device 10 may incorporate other features that assist in providing a therapeutic result. For example, certain therapies may be optimized if the active elements of the device are in a particular position, and other therapies may be optimized if the individual's head is in a particular position. For this situation, the device may include an inclinometer that measures the angle at which the individual's head is positioned in relation to a known norm. In a preferred embodiment, the device incorporates an incline indicator to show the individual or a health care provider the current angle at which an individual's head is positioned. Naturally, the inclinometer includes a calibration device to adjust for a particular individual's natural head position.

The device disclosed herein incorporates standard features that are commonly used in hearing aids and other inner ear devices known today. For instance, given the fact that vestibular stimulation will likely not be administered around the clock, the device incorporates an automatic shutdown mode enabled during extensive periods of inactivity. Other useful features available for the device include battery operation and padding for the outer portion worn on the outer ear. The housing 50 for the computerized control module 70 may be available in stylized and appropriately colored models to accommodate the tastes of the individual wearing it.

The foregoing is illustrative of the present invention, and is not to be construed as limiting thereof. The invention is defined by the following claims, with equivalents of the claims to be included therein.

That which is claimed is:

1. An in-ear device for delivering caloric vestibular stimulation to an individual, comprising:
   (a) an ear insert so dimensioned as to be insertable into the ear canal of the individual, said ear insert having an inner portion;
   (b) at least one thermoelectric transducer mounted on said ear insert inner portion; and
   (c) a sleeve connected to said ear insert inner portion and overlying said at least one thermoelectric transducer, said sleeve further having an inner surface portion configured to conformably engage said ear insert inner portion and an outer surface portion configured to conformably engage the ear canal, so that heat is transferred between said transducer and the ear canal through said sleeve to deliver vestibular stimulation to the individual.

2. The device of claim 1, wherein said sleeve comprises portions of varying thermal conductivity such that the sleeve controls the rate of heat transfer between said transducer and a particular portion of the ear canal.

3. The device of claim 1, wherein said sleeve distributes the heat transfer substantially evenly over at least a portion of the ear canal.

4. The device according to claim 1, wherein said caloric vestibular stimulation comprises an increase in temperature of the ear canal.

5. The device according to claim 1, wherein said caloric vestibular stimulation comprises a reduction in the temperature of the ear canal.

6. The device according to claim 1, further comprising at least one electrode mounted on said ear insert inner portion, wherein said at least one thermoelectric transducer and said at least one electrode occupy adjustable positions on said insert to provide controlled vestibular stimulation directed to a particular area of the vestibular system.

7. The device of claim 1, wherein said ear insert inner portion has a shape that corresponds to the ear canal of the individual.

8. The device of claim 1, wherein said sleeve outer surface portion has a shape that corresponds to the ear canal of the individual.

9. The device of claim 1, wherein said ear insert has an outer portion, said outer portion configured to overlie at least a portion of the external ear of an individual.

10. The device of claim 1, wherein said ear insert is configured to be positioned completely within the ear canal of the individual.

11. The device of claim 1, wherein said at least one thermoelectric transducer comprises at least two separately controllable thermoelectric transducers spaced apart from one another on said ear insert inner portion.

12. The device of claim 11, further comprising a controller configured to heat at least one of said at least two separately controllable thermoelectric transducers and to cool at least one other of said at least two separately controllable thermoelectric transducers.

13. The device of claim 1, wherein each of said at least one thermoelectric transducers is a thin film thermoelectric transducer.

14. The device of claim 1, wherein said ear insert further comprises an external transducer operatively associated therewith and configured for positioning on or adjacent the mastoid process of the individual for delivering thermal, electric or mechanical stimuli to the individual.

15. The device of claim 1, wherein said ear insert has a canal formed therein to facilitate ventilation of the ear; and wherein said ear insert further comprises an acoustic transducer operatively associated therewith for delivering auditory stimuli to the individual.

16. The device of claim 1, wherein said sleeve has a thermal conductivity of from 0.1 to 50 W/m×K and a hardness of from 0 to 50 on the Shore A scale.

17. A method of delivering caloric vestibular stimulation to an individual, comprising:
(i) positioning a device of claim 1 in the ear canal of an individual, and then;
(ii) activating said at least one thermoelectric transducer for a time and to a temperature sufficient to deliver caloric vestibular stimulation to the individual.

18. The method of claim 17, wherein said at least one thermoelectric transducer comprises at least two separately controllable thermoelectric transducers spaced apart from one another on said ear insert inner portion, and wherein said activating step comprises separately and selectively activating said at least two separately controllable thermoelectric transducers.

19. The method of claim 18, wherein at least one of said at least two separately controllable thermoelectric transducers is heated and at least one other of said at least two separately controllable thermoelectric transducers is cooled.

20. An in-ear device for delivering caloric vestibular stimulation to an individual, comprising:
(a) a preformed ear insert so dimensioned as to be insertable into the ear canal of an individual, said insert having an inner portion; and
(b) at least two separately controllable thermoelectric transducers spaced apart from one another on said ear insert inner portion,
said preformed ear insert having a surface portion configured to conformably engage the ear canal, so that heat can be conducted between each of said at least two separately controllable thermoelectric transducers and the ear canal to deliver vestibular stimulation to the individual.

21. The device of claim 20, wherein said ear insert has an outer portion, said outer portion configured to overlie at least a portion of the external ear of an individual.

22. The device of claim 20, wherein said ear insert is configured to be positioned completely within the ear canal of the individual.

23. The device of claim 20, further comprising a controller configured to heat at least one of said at least two separately controllable thermoelectric transducers and to cool at least one other of said at least two separately controllable thermoelectric transducers.

24. The device of claim 20, wherein each of said at least two separately controllable thermoelectric transducers is a thin film thermoelectric transducer.

25. The device of claim 20, wherein said ear insert further comprises an external transducer operatively associated therewith and configured for positioning on or adjacent the mastoid process of the individual for delivering thermal, electric or mechanical stimuli to the individual.

26. The device of claim 20, wherein said ear insert has a canal formed therein to facilitate ventilation of the ear; and said ear insert further comprises an acoustic transducer operatively associated therewith for delivering auditory stimuli to the individual.

27. The device of claim 20, wherein said ear insert comprises a compressible material.

28. A method of delivering caloric vestibular stimulation to an individual, comprising:
(i) positioning a device according to claim 20 in the ear canal of the individual, and then;
(ii) activating at least one of said at least two separately controllable thermoelectric transducer for a time and to a temperature sufficient to deliver caloric vestibular stimulation to the individual.

29. The method of claim 28, wherein said activating step comprises separately and selectively activating each of said at least two separately controllable thermoelectric transducers.

30. The method of claim 28, wherein at least one of said at least two separately controllable thermoelectric transducers is heated and at least one other of said at least two separately controllable thermoelectric transducers is cooled.

31. A method of delivering vestibular stimulation to an individual's brain, the method comprising:
arranging a thermal transducer and an electrode on an ear insert in a position to stimulate the vestibular system of the individual;
electronically connecting said transducer and said electrode to a controller;
supplying said controller with galvanic skin resistance data and temperature data from the individual;
activating said transducer and said electrode via a controller for a time and to a temperature sufficient to deliver vestibular stimulation to the individual, wherein the vestibular stimulation is selected from the group comprising caloric stimulation, electrical stimulation, and combinations of each.

32. The method according to claim 31, further comprising the step of measuring physiological changes in the individual, wherein said physiological changes are selected from the group consisting of brain chemistry changes and blood chemistry changes.

33. The method according to claim 31, further comprising the step of measuring physiological changes in the individual, wherein said physiological changes are selected from the group consisting of circadian temperature cycle time shifts, ascorbic acid production, serotonin production, acetylcholine production, histamine production, and heat shock protein production.

* * * * *